(12) United States Patent
Hopman et al.

(10) Patent No.: US 6,611,705 B2
(45) Date of Patent: Aug. 26, 2003

(54) WIRELESS ELECTROCARDIOGRAPH SYSTEM AND METHOD

(75) Inventors: Nicholas C. Hopman, Lake Zurich, IL (US); Daniel L. Williams, Norwell, MA (US); Franco Lodato, Weston, FL (US)

(73) Assignee: Motorola, Inc., Schaumburg, IL (US)

( * ) Notice: Subject to any disclaimer, the term of this patent is extended or adjusted under 35 U.S.C. 154(b) by 0 days.

(21) Appl. No.: 09/908,509

(22) Filed: Jul. 17, 2001

(65) Prior Publication Data

US 2002/0072682 A1 Jun. 13, 2002

Related U.S. Application Data

(60) Provisional application No. 60/219,082, filed on Jul. 18, 2001.

(51) Int. Cl.[7] .............................................. A61B 5/0402
(52) U.S. Cl. ..................................... 600/509; 600/386
(58) Field of Search ........................ 600/382, 386–394, 600/508–521; 607/149

(56) References Cited

U.S. PATENT DOCUMENTS

| 3,998,213 | A | * | 12/1976 | Price |
| 4,909,260 | A | | 3/1990 | Salem et al. |
| 4,957,109 | A | | 9/1990 | Groeger et al. |
| 4,981,141 | A | | 1/1991 | Segalowitz |
| 5,353,793 | A | | 10/1994 | Bornn |
| 5,394,879 | A | | 3/1995 | Gorman ...................... 128/707 |
| 5,400,794 | A | | 3/1995 | Gorman ...................... 128/696 |
| 5,538,007 | A | | 7/1996 | Gorman ...................... 128/710 |
| 5,628,326 | A | | 5/1997 | Arand et al. |
| 5,634,468 | A | | 6/1997 | Platt et al. |
| 5,669,391 | A | | 9/1997 | Williams |
| 5,704,351 | A | * | 1/1998 | Mortara et al. |
| 5,862,803 | A | | 1/1999 | Besson et al. |
| 5,913,827 | A | | 6/1999 | Gorman ...................... 600/509 |
| 5,938,597 | A | | 8/1999 | Stratbucker |
| 5,957,854 | A | | 9/1999 | Besson et al. |
| 6,208,889 | B1 | | 3/2001 | Gorman ...................... 600/520 |
| 6,289,238 | B1 | | 9/2001 | Besson et al. |
| 6,292,687 | B1 | * | 9/2001 | Lowell et al. |
| 6,304,774 | B1 | | 10/2001 | Gorman ...................... 600/520 |
| 6,332,094 | B1 | | 12/2001 | Gorman ...................... 600/520 |
| 6,441,747 | B1 | | 8/2002 | Khair et al. |

FOREIGN PATENT DOCUMENTS

| WO | WO 94/01039 | 1/1994 |
| WO | WO 00/62667 | 10/2000 |

* cited by examiner

Primary Examiner—Scott M. Getzow
(74) Attorney, Agent, or Firm—Brinks Hofer Gilson & Lione

(57) ABSTRACT

A method and system for wireless ECG monitoring is provided. An electrode connector, transmitter and receiver operate with existing electrodes and ECG monitors. The electrode connector includes connectors for attaching to disposable or reusable single electrodes. The transmitter transmits the signals from the electrodes to the receiver. The receiver passes the electrode signals to the ECG monitor for processing. ECG monitors used with an electrical conductor, for example wire connections to electrodes, are connected with the receiver, avoiding the purchase of a new monitor. Any legacy ECG monitor, including different ECG monitors, connects with the receiver using the ECG monitor's lead-wires. The ECG monitor operates as if directly connected to the electrodes without the problems discussed above associated with wires running from the ECG monitor to the patient.

51 Claims, 5 Drawing Sheets

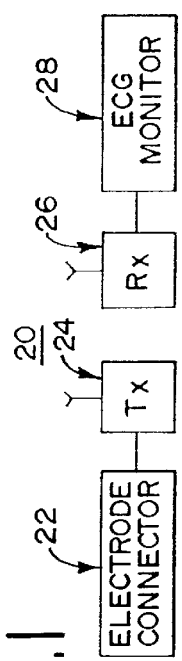
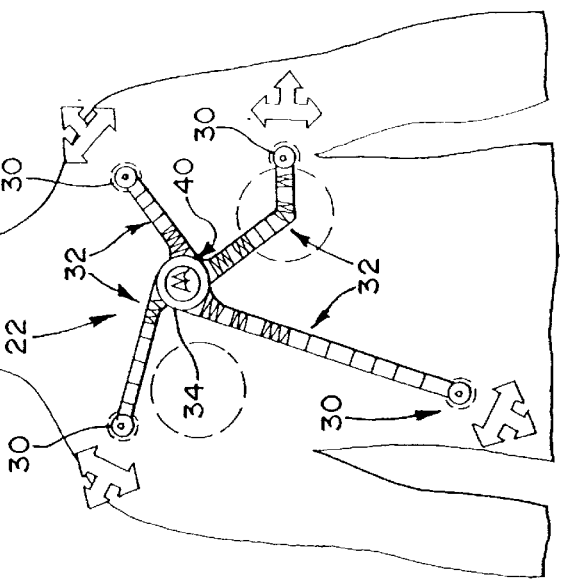
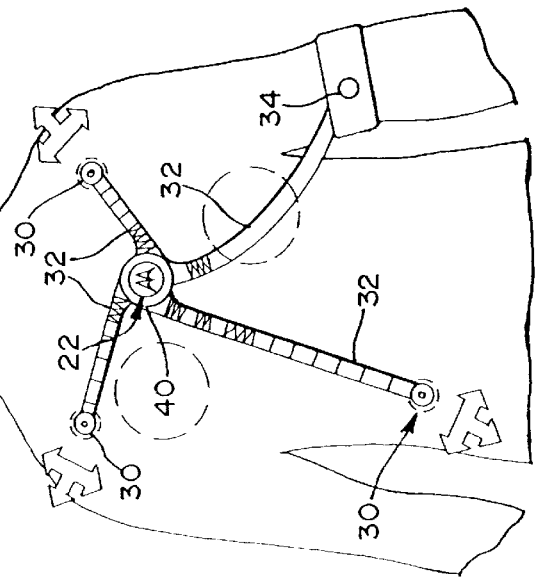

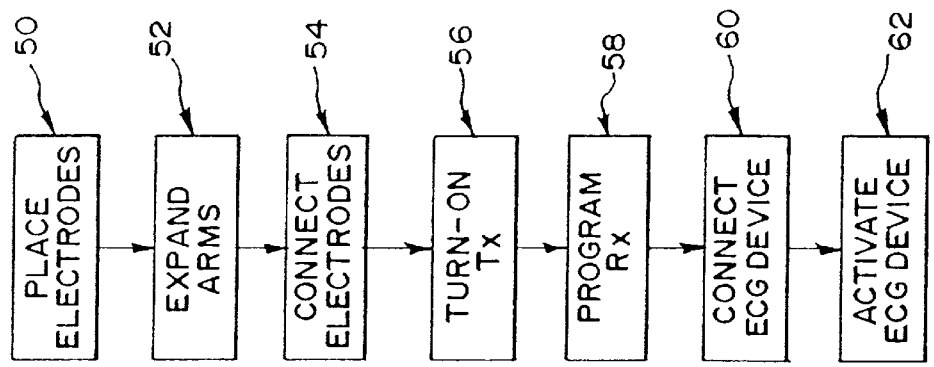
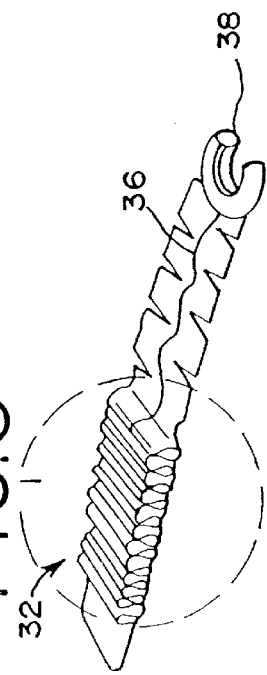
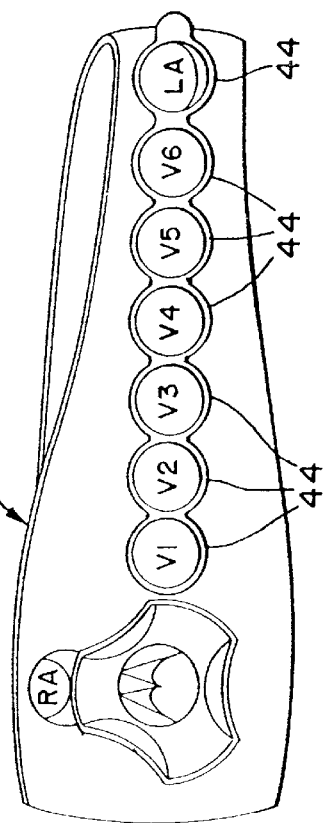

WIRELESS ELECTROCARDIOGRAPH SYSTEM AND METHOD

RELATED APPLICATIONS

This application is a continuation-in-part of and claims the benefit of the filing date pursuant to 35 U.S.C. §119(e) of Provisional Application Serial No. 60/219,082, filed Jul. 18, 2001, for a WIRELESS EKG, the disclosure of which is hereby incorporated by reference.

BACKGROUND

This invention relates to medical monitoring systems and methods. In particular, a biomedical system and method for monitoring a patient is provided.

Biomedical monitoring systems include bedside, transportable, ambulatory and discrete vital sign monitors. In vital signs monitors, electrocardiograph (ECG), temperature, blood pressure or other characteristics of a patient are monitored.

ECG systems are used for monitoring activity of a patient's heart. For example, three electrodes are positioned on the patient. The signal from one electrode is used as a reference signal for a difference between the signals of two other electrodes (e.g. ECG vector). By using this reference signal, and a differential amplifier configuration, common mode interference can be essentially eliminated or reduced. As another example, nine electrodes are positioned on the patient for a "12-lead" analysis of electrical activity of the heart.

Wires are connected from the electrodes to an ECG monitor. The ECG monitor processes the signals and outputs ECG data, such as a plurality of traces representing activity of the heart by measuring electrical signals at different positions on the patient. However, the wires inhibit movement by and around the patient. The wires will stress the electrodes, resulting in malfunction or disconnection from the patient. A caregiver's time is then required to reconnect or replace the electrodes. Patients are often moved during a day, requiring disconnecting one ECG monitor and reconnecting another ECG monitor. Often the electrodes also need to be removed and replaced. If not replaced in exactly the same position, the patient's ECG will be different from ECG monitor to ECG monitor, creating an artifact in the ECG.

Wireless ECG systems connect the electrodes to a transmitter to avoid wires from the patient to a monitor. In the example described in WO 94/01039, a microchip is positioned proximate the electrodes on the patient. The microchip analyzes the signals from the electrodes and transmits the results (see page 42). The results are received and provided to a printer or monitor (see page 26). However, a complete system including a monitor, printer or recorder operable to receive the signals as processed by the microchip on the patient is required.

Holter monitors record a patient's vital signs over a time period. The patient carries the complete monitor and recorder. The information can be downloaded or otherwise obtained for subsequent analysis. However, many of these systems limit the bandwidth of signals to suppress artifacts associated with patient movement, so information can be lost. Special monitors or other devices may be required for obtaining the stored data for analysis, preventing maximum use of other equipment.

Wireless ECG systems often use patches or strips for positioning electrodes. The strip is fabricated with a plurality of electrodes electrically connected to the transmitter. If one electrode fails, the entire strip is replaced.

BRIEF SUMMARY

The present invention is defined by the following claims, and nothing in this section should be taken as a limitation on those claims. By way of introduction, the preferred embodiment described below includes a method and system for wireless ECG monitoring.

An electrode connector, transmitter and receiver operate with existing electrodes and ECG monitors. The electrode connector includes connectors for attaching to disposable or reusable single electrodes. The transmitter transmits the signals from the electrodes to the receiver. The receiver passes the electrode signals to the ECG monitor for processing. ECG monitors used with an electrical conductor, for example wire connections to electrodes, are connected with the receiver, avoiding the purchase of a new monitor. Any legacy ECG monitor, including different ECG monitors, connects with the receiver using the ECG monitor's leadwires. The ECG monitor operates as if directly connected to the electrodes without the problems discussed above associated with wires running from the ECG monitor to the patient.

In a first aspect of the invention, an electrode connector for ECG monitoring of a patient is provided. Material is operable to interconnect a plurality of electrodes. The material includes a plurality of electrode releasable connectors.

In a second aspect, a method for connecting electrodes for ECG monitoring is provided. A plurality of electrodes are placed. A plurality of expandable arms, one expandable arm provided for each of the plurality of electrodes, are expanded. The plurality of expandable arms are connected to the plurality of electrodes.

In a third aspect, a system for monitoring electrical signals generated by a patient is provided. A transmitter is operable to transmit electrode signals. A receiver is responsive to the transmitter to generate the electrode signals. The receiver has an output connector operable to connect with electrode wires of an ECG monitor.

In a fourth aspect, a method for monitoring electrical signals generated by a patient is provided. Signals are received from electrodes. Information representing the signals received from electrodes is transmitted. The information is received. The signals received from the electrodes are reconstructed. Existing wires from an ECG monitor are connected. The reconstructed signals are received at the ECG monitor.

In a fifth aspect, a wireless ECG monitoring system for reconstructing signals at a plurality of electrodes is provided. An electrode connector is operable to connect with the plurality of electrodes. A single transmitter is operable to connect with the electrode connector. The single transmitter is operable to transmit signals from the plurality of electrodes. A receiver is operable to reconstruct the signals from the plurality of electrodes.

In a sixth aspect, a method for wireless ECG monitoring with reconstructed signals from a plurality of electrodes is provided. The plurality of electrodes are connected with an electrode connector. Signals from the plurality of electrodes are transmitted with a single transmitter. The signals transmitted by the transmitter are received. The signals from the plurality of electrodes are reconstructed.

Further aspects and advantages of the invention are discussed below in conjunction with the preferred embodiments.

BRIEF DESCRIPTION OF SEVERAL VIEWS OF THE DRAWINGS

FIG. 1 is a block diagram of one embodiment of an ECG monitoring system.

FIG. 3 is a perspective view of one embodiment of an expandable arm of the electrode connectors of FIGS. 2A–D.

FIG. 4 is a front view of one embodiment of a belt used with the electrode connector of FIG. 2D.

FIG. 5 is a flow chart of one embodiment for operation of the ECG monitoring system of FIG. 1.

DETAILED DESCRIPTION OF THE PREFERRED EMBODIMENTS

A wireless ECG system uses existing electrodes and ECG monitors. The wireless ECG system wirelessly bridges between conventional electrodes on a patient and a conventional ECG monitor. The wireless ECG system is an accessory that augments the capability of conventional, or legacy, ECG monitors or systems. The wireless ECG system functions as a wireless extension cord that physically un-tethers a patient from a conventional lead-wire cable connected to a conventional ECG monitor.

The wireless ECG system includes three components: an electrode connector (e.g. sensor array), a transmitter (e.g. ECG-radio) and a receiver (e.g. base station). These components interpose between conventional electrodes worn by a patient and a conventional lead-wire cable of a conventional ECG monitor without requiring any additional changes to the conventional electrodes, the conventional lead-wire cables, or the conventional ECG monitoring systems. An electrode connector with releasable connections, such as snap terminals, and expandable arms electrically connects with existing electrodes, such as snap terminal type electrodes. A transmitter provides signals received from the electrodes to the receiver. The receiver connects to the ECG monitor via conventional lead-wires or electrode wires of the ECG monitor. Signals representing the electrode signals measured or sampled on a patient are provided to the ECG monitor. The existing ECG monitor processes the signal to output ECG data, such as ECG vector data. Consequently, physical coupling between the patient and the electrocardiograph or vital signs monitor is eliminated. This enables the patient to freely ambulate while being monitored by the ECG.

Figure 6:
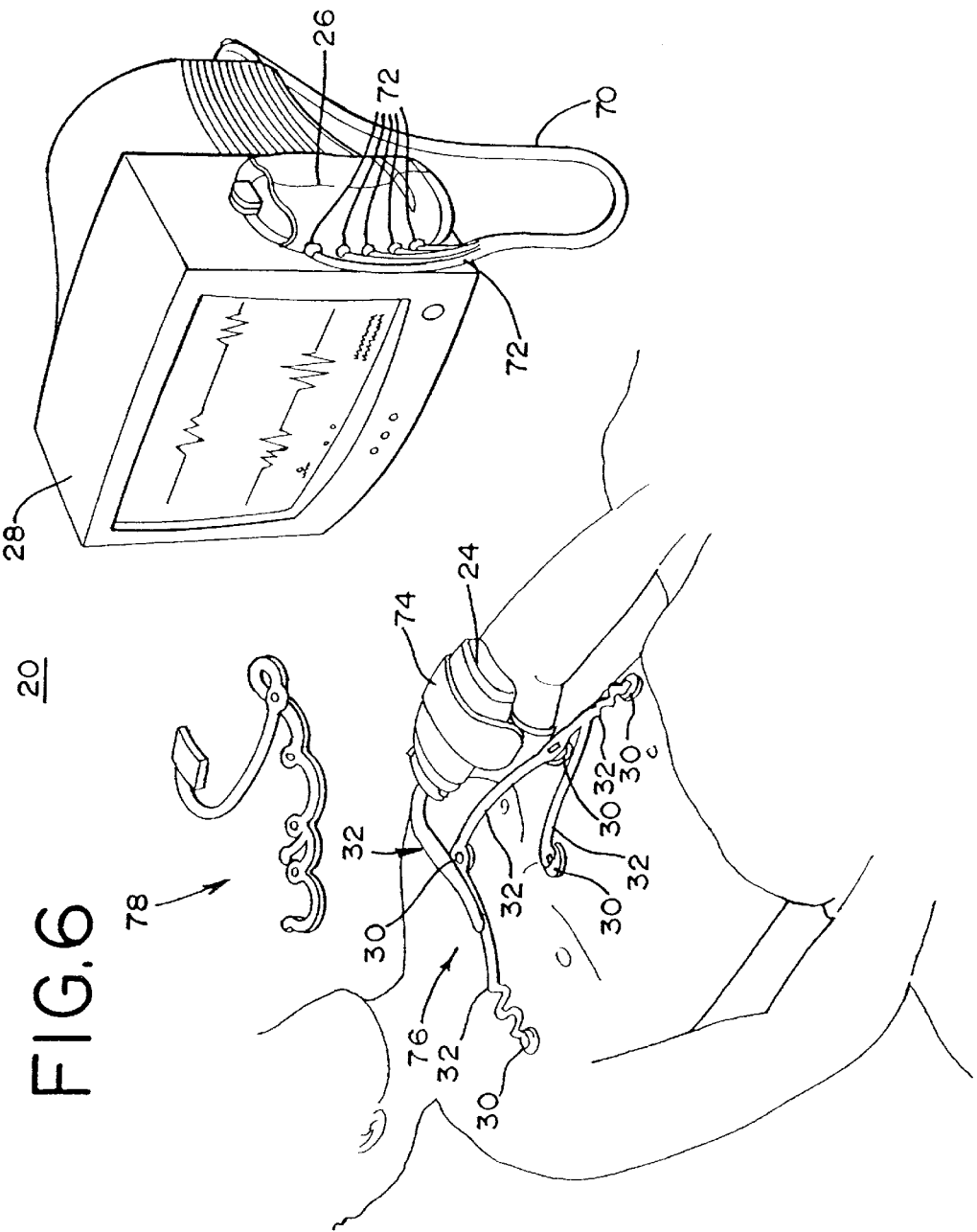
FIG. 6 is a perspective view of another embodiment of an ECG monitoring system.

FIGS. 1 and 6 show a wireless ECG monitoring system 20. The ECG monitoring system 20 includes an electrode connector 22, a transmitter 24, a receiver 26 and an ECG monitor 28. Additional or fewer components can be used, such as providing the system 20 without the ECG monitor. Alternative components can be used, such as a strip or patch with electrodes rather than an electrode connector 22 or a printer rather than an ECG monitor 28.

Figure 2D:
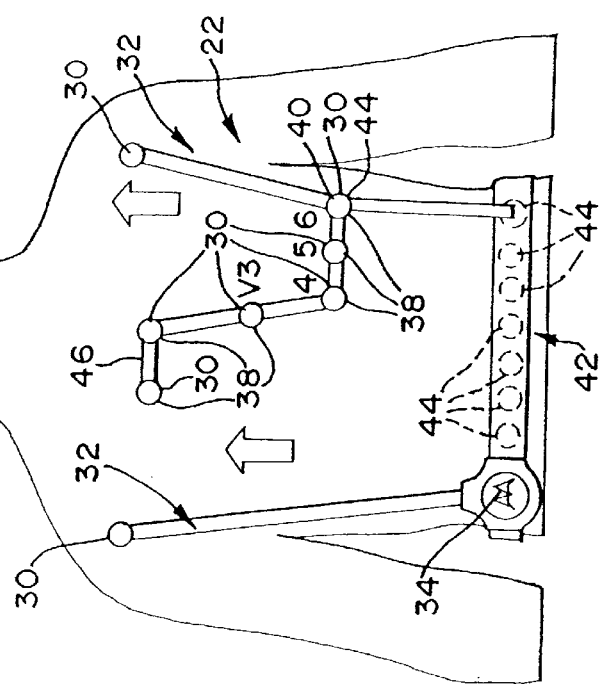
FIGS. 2 A–D are front views of various embodiments of electrode connectors and transmitters of the ECG monitoring system of FIG. 1.
Figure 2C:
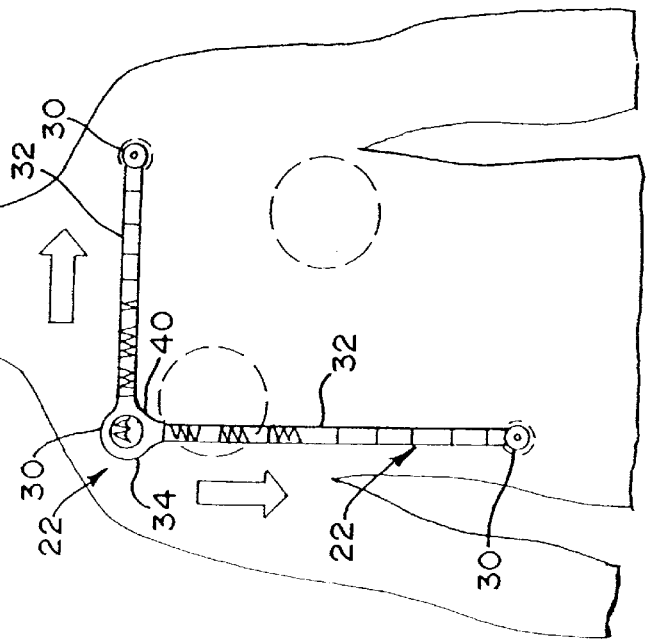

FIGS. 2A–D show electrode connectors 22 of various embodiments used with an array of electrodes 30. The electrodes 30 comprise conductive material. For example, a foam disk with a conductive fabric or a fabric with a conductive metal layer is used. The electrodes 30 include a snap terminal (male, female or both) or tab for connection to a wire. Other connectors may be provided on the electrodes 30. The electrodes 30 are positioned for ECG monitoring, such as positioned for hexaxial-lead monitoring as illustrated in FIGS. 2A–C. For hexaxial-lead monitoring, the electrodes 30 are positioned in left and right arm positions and right and/or left leg positions. With these electrode positions, up to seven leads can be monitored (e.g. Lead I, II, III, aVL, aVR, aVF and chest positions). Other positions of electrodes can be used, such as associated with precordial (e.g. V1–V6) or combinations of hexaxial and precordial (e.g. "12-lead" monitoring). The electrodes 30 are attached to the patient with conductive hydrogel or other adhesives. The electrodes 30 and/or the electrode connector 22 are disposable or reusable.

The electrode connector 22 includes a plurality of expandable arms 32 and a transmitter 24. The expandable arms 32 comprise polypropylene or polyethylene fabric with an electrically conductive element such as a wire 36 and an electrode joiner 38 as shown in FIG. 3. In one embodiment, the expandable arm 32 is formed from Kapton or Mylar, manufactured by DuPont, a cloth, a fabric or another flexible material. Multiple layers of dielectric, and or electrically or magnetically conductive material can be used to shield the wire 36. Alternatively, no shielding is provided. Fabric or other material can be attached to one or both sides of the expandable arm 32, such as to provide comfort for a patient.

The expandable arm 32 of one embodiment comprises memoryless material, such as the materials discussed above. The expandable arm 32 is die cut in a serpentine pattern as shown in FIG. 3. The expandable arm 32 expands by releasing or breaking connections between portions of the serpentine pattern. When expanded, a portion or all of the expandable arm 32 is extended. Where only a portion of the expandable arm 32 is extended, another portion remains folded or unbroken. Pressure on the electrode 30 from elastic or stretchable material is avoided, providing for more stable connection of the electrode 30 to the patient. The expandable arm 32 also allows for extension as needed without extra extension and resulting loose material to be tangled or provide discomfort. In alternative embodiments, a stretchable or elastic expandable arm 32 is used. In yet other alternative embodiments, a non-expandable arm is used.

The electrical conductor or wire 36 in the expandable arm 32 preferably comprises a conductor printed on the Mlyar, Kapton or other flexible dielectric material. The printed conductor is flexible, providing electrical connection between the electrode 30 and the transmitter 24 whether expanded or unexpanded. In alternative embodiments, the wire 36 comprises a thread of copper or another conductive material. In yet other embodiments, the wire comprises a coaxial cable. One or more wires 36 are provided for each electrode 30. For some expandable arms 32, one wire 36 electrically connects from one electrode 30 to the transmitter 24 or another expandable arm 32. For other expandable arms 32, a plurality of wires 36 connect from a respective plurality of electrodes 30 on the same and/or another expandable arm 32.

The electrode joiner 38 comprises a clip (e.g. alligator clip), snap terminal, or connector (male, female or both), adhesive tab or other device for electrically and physically joining the electrode 30 to the expandable arm 32. As shown in FIG. 2D, a plurality of electrode joiners 38 can be used on one expandable arm 32. In other embodiments, one electrode joiner 38 is provided at an end or other portion of the expandable arm 32. If one electrode 30 malfunctions, only the electrode 30 is removed and replaced. The electrode connector 22 is kept.

The other end of the expandable arm 32 connects with other expandable arms 32 or the transmitter 24. The plurality of expandable arms 32 are connected in any of various configurations, such as a spiral configuration shown in FIGS. 2A and 2B. The expandable arms 32 releasably or fixedly connect from a hub 40. In the embodiment of FIG. 2A, one expandable arm 32 includes wires for all or a sub-set of the electrodes 30 to electrically communicate with the transmitter 24. The transmitter 24 is spaced away from the hub 40, such as being positioned on an arm band (shown), or on another location on the patient. For example, FIG. 6 shows the transmitter 24 held to the patient with an arm band 74 comprising neoprene or other fabric. In the embodiment of FIG. 2B, the transmitter 24 is positioned on the hub 40.

The hub 40 comprises the same material as the expandable arms 40, such as from using a continuous sheet to form the hub 40 and expandable arms 32. In other embodiments, the hub 40 comprises the same or different material with releasable connectors for electrically and physically connecting with the expandable arms 32. For example, the hub 40 comprises plastic or other material with plurality of conductive snap terminals for connecting with the expandable arms.

Another configuration is a "7" or "L" configuration, such as the embodiment shown in FIG. 2C. One of the electrode positions generally corresponds to the hub 40, and expandable arms 32 expand from the hub 40.

Other alternative configuration embodiments include "C" or "U" shapes with multiple hubs.

Yet another configuration is shown in FIG. 2D. A belt 42 connects with a plurality of expandable arms 32. The belt 42 comprises neoprene, non-woven polypropylene or polyethylene fabric or other materials. One or more pockets or connectors for the transmitter 24, other electrical components, batteries, displays, or other devices are provided on the belt 42. In one embodiment shown in FIG. 4, the belt 42 is formed to fasten or stretch around a waist of the patient, but arm, neck, chest or leg belts can be used. One or more of the expandable arms 32 releasably connects with the belt 40. In one embodiment, the belt 40 includes separate connectors 44 for each electrode position. In other embodiments, one or more of the connectors 44 on the belt 40 include separate electrical contacts for electrically connecting with multiple wires 36 and associated electrodes 30 on one expandable arm 32. The connectors 44 are provided on the outer surface of the belt 42, but can be provided in pockets. The transmitter 24 is positioned on the belt 42 or elsewhere on the patient.

As shown in FIG. 2D, one or more of the expandable arms 32 may include one or more connectors 44 for connecting with other expandable arms 32, forming a hub 40. For example, an electrically conductive snap terminal or terminals connect the expandable arms. Other connectors, such as male and female housings with clips and wires associated with connecting multiple separate wires between the expandable arms, can be used.

The configuration is associated with the desired ECG monitoring. FIGS. 2A–C illustrate hexaxial positions for the electrodes 30, such as associated with continuous monitoring. Electrodes 30 are positioned at hexaxial positions associated with left arm, right arm, left leg and/or right leg. Many ECG systems use three electrode positions, but some use four or more. FIGS. 2A and 2C show three electrode positions. FIG. 2B shows four electrode positions. More or fewer electrode positions, such as three to five positions, may be provided with additional electrode joiners 38 and/or expandable arms 32.

FIG. 2D shows both hexaxial and precordial positions for the electrodes 30, such as associated with "12 lead" ECG monitoring. Two or more expandable arms 32 connect with electrodes 30 in hexaxial positions. One or more expandable arms 32, such as expandable arm 46, connect with electrodes 30 in precordial positions. In this embodiment, the precordial expandable arm 46 connects with another of the expandable arms 32 used for hexaxial positions. The resulting hub 40 is associated with one of the precordial electrode positions. In alternative embodiments, the hub 40 is spaced away from any electrode 30. In yet other alternative embodiments, the precordial expandable arm or arms 46 separately connect with the belt 42. For example, separate hexaxial and precordial electrode connectors 76 and 78 are provided as illustrated in FIG. 6. The precordial electrode connector 78 connects with the hexaxial electrode connector 76 or the transmitter 24.

The hubs 40 and expandable arms 32 may include connectors 44 for adding additional expandable arms 32 or electrodes 30. For example, two or more expandable arms 32 are positioned for hexaxial-lead monitoring as shown in FIG. 2D without the precordial expandable arm 46. When precordial-lead monitoring is desired, electrodes 30 are positioned along six precordial positions, and the expandable arm 46 is expanded and connected with the precordial electrodes 30. The expandable arm 46 is also connected to the belt 42 or other expandable arm 32. Alternatively, different electrode connectors 22 are used for different ECG systems or numbers of electrodes. Since the expandable arms 32 are flexible and expandable, the same electrode connector 22 is used for various electrode positions as represented by the bold arrows in FIGS. 2A–D.

The transmitter 24 receives the signals from the electrodes 30. The transmitter 24 comprises a wireless transmitter or transceiver, such as a radio, ultrasound, infrared or other transmitter. For example, a transceiver operable according to Bluetooth specifications (i.e. a Bluetooth transceiver) is used. In one embodiment, the transmitter 24 comprises an application specific integrated circuit, a processor or other circuit.

Figure 7:
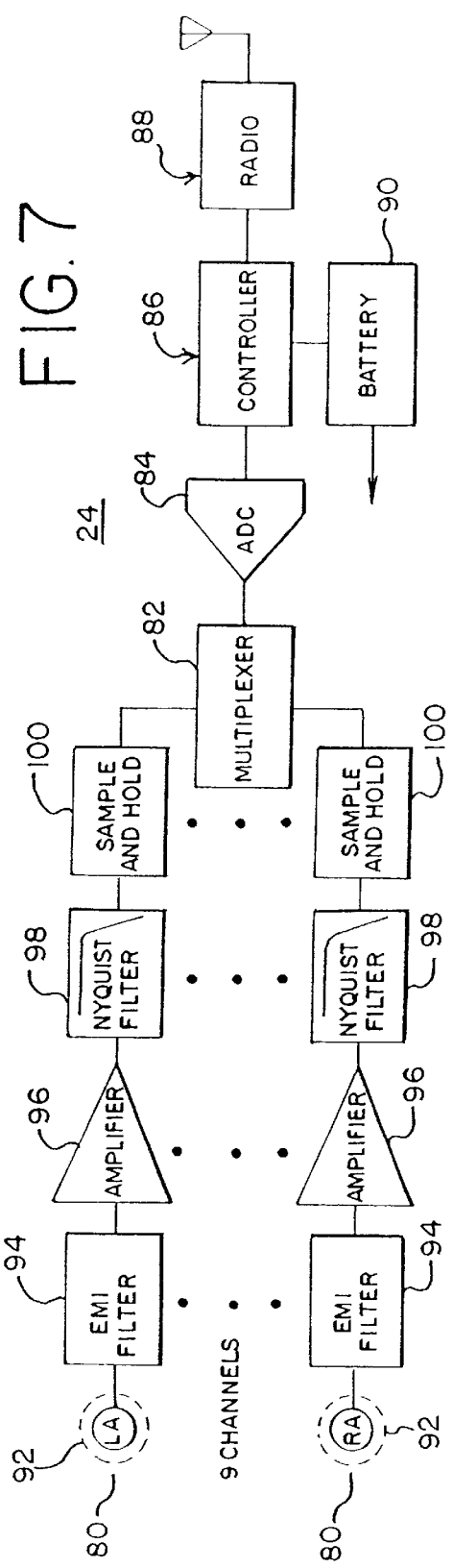
FIG. 7 is a block diagram of one embodiment of a transmitter.

FIG. 7 shows one embodiment of the transmitter 24. The transmitter 24 includes a plurality of electrode signal channels 80, a multiplexer 82, an analog-to-digital converter (ADC) 84, a controller 86, a radio 88 and a battery 90. Additional, fewer or different components can be used. The battery 90 comprises a replaceable or rechargeable lithium battery connected to provide power to the various components of the transmitter 24.

In one embodiment, nine electrode signal channels 80 corresponding to the typical nine electrodes used for hexaxial-lead and precordial-lead monitoring are provided. Fewer or additional electrode signal channels 80 can be provided. The electrode signal channels 80 each comprise a connector 92, a filter 94, an amplifier 96, a Nyquist filter 98 and a track and hold circuit 100. The connector 92 comprises snaps, plugs or other electrical connectors for connecting with the wires 36. The filter 94 comprises a low pass filter, such as for removing electromagnetic interference signals. The amplifier 96 amplifies the signals from the electrodes 30. The Nyquist filter 98 comprises a low pass filter for removing high frequency content of the amplified signals to avoid sampling error. The track and hold circuit 100 enables the system to sample all 9 channels of signals at a same or relative times so that there is no differential error created when these signals are combined later in a legacy ECG monitor.

The multiplexer 82 sequentially selects signals from the electrode signal channels 80 using time division multiplexing, but other combination functions can be used. The ADC 84 converts the combined analog signals to digital signals for transmission. The controller 86 controls operation of the various components and may further process the digital signals, such as diagnosing operation, controlling any user interface (e.g. input and/or output devices), and detecting connection to electrodes. Preferably the controller comprises a digital signal processor (DSP) that decimates the digitized signals so as to lessen the bandwith required to transmit the signals. The radio 88 modulates the digital signals with a carrier signal for transmission. In one embodiment, the radio 88 includes a demodulator for receiving information. The controller 86 processes the received information.

In one embodiment, the transmitter 24 is operable to minimize introducing undesired noise or signals. For example, components are matched such that later application to a differential amplifier in a legacy ECG monitor for determining a heart vector inaccurate. In one embodiment, the ECG vectors are not formed by the ECG system 20, but rather by the legacy ECG monitor. Because the ECG system 20 is essentially "in-series" with the legacy ECG monitor, any error may produce undesirable results. One potential source of error is differential error. This differential error can be observed on the legacy ECG monitor when the ECG monitor forms the ECG lead signals by combining the individual electrode signals in the ECG monitor input stage. This input stage comprises a difference, or differential, amplifier to eliminate common mode interference from the signals produced at the electrodes 30. If there is any difference in how each of the electrode signals are processed, when the legacy ECG's differential amplifier forms the ECG lead signals or ECG vectors an artifact will be present. For example, in the transmitter 24 if there is a difference in the gain of the amplifiers, a difference in the phase shift associated with the anti-aliasing (Nyquist) filters, a difference in how the respective track and hold circuits treat the electrode signals, this differential error creates an artifact on the legacy ECG monitor. One important technique to minimize this potential source of differential error, is to choose a Nyquist filter 98 cutoff frequency that is very high. This is because each individual filter will have differing group delay performance, and to mitigate that difference the frequency that this group delay will affect is much higher than the frequency of the ECG signals, which are about 0.05 Hz to 150 Hz. By choosing a high cutoff frequency for the Nyquist filters 98, any mismatch in the Nyquist filter 98 components will not affect accuracy of the individual electrode ECG signals.

For example picking a filter cutoff frequency of 1,200 Hz mitigates this source of error. With this approach, the individual electrode ECG signals are oversampled at about 3,000 Hz in order to not introduce aliasing. Of course higher filter cutoff frequencies and correspondingly higher sampling rates may further reduce error. Lower cutoff frequencies and/or sampling rate may be used.

Because the electrode signals are now sampled at such a high rate, these signals may be decimated to minimize the required transmission bandwidth. For example the digital samples are decimated by a factor of 8 in the controller 86. Greater or lesser rates of decimation can be used, such as decimation as a function of the bandwidth available for transmission, the number of electrode signals to be represented, and the Nyquist sampling rate. In alternative embodiments, the digital data is compressed, the electrode signals are not oversampled, or no decimation is provided.

The selected signals are transmitted as radio or other signals modulated with a carrier signal. Various formats for transmission can be used, such as Bluetooth, TCP/IP, or other formats. The controller 86 controls the acquisition and transmission of the electrode signals. The transmitted signals comprise data representing the signals received from the electrodes 30. In alternative embodiments, the controller 86 may also processes the signals prior to transmission, so the transmitted signals comprise ECG vector data. In one embodiment, the transmitter 24 also receives control information from the receiver 26, such as instructions to resend signals.

The transmitter 24 is positioned near the patient. In the embodiment shown in FIGS. 2A and 2C, the transmitter 24 is positioned on the hub 40 or an expandable arm 32. In the embodiment shown in FIG. 2B, the transmitter 24 is positioned on an arm band, but leg, chest or other bands can be used. In the embodiment of FIG. 2D, the transmitter 24 is positioned on the belt. Either a pocket or a surface mount is provided for the transmitter 24. In alternative embodiments, the transmitter 24 is positioned in a pocket of clothing or elsewhere on the patient.

In one embodiment, the transmitter 24 is removable. For example, clips, screws, bolts, latches or other devices releasably hold the transmitter 24 in contact with the electrode connector 22. Electrical contact is provided by connectors operable to withstand electrical energy produced by a defibrillator. These connectors may also provide the physical connection. The transmitter 24 is removed for recharging the battery or a plug is provided on the electrode connector 22 or the transmitter 24 for recharging the battery without removal. The battery or the transmitter 24, like the electrode connector 22, can be used for multiple days or multiple times and is separately disposable to avoid costly replacement of the entire system 20.

Referring to FIGS. 1 and 6, the receiver 26 receives the transmitted signals. The receiver 26 comprises a radio, infrared, ultrasound or other receiver. An application specific integrated circuit, digital signal processor or other circuit for receiving signals from the transmitter 24, decoding the received signals, and generating representative electrode signals is used. In one embodiment, the receiver comprises a transceiver for two-way communication with the transmitter 24. For example, a transceiver operable pursuant to the Bluetooth specification is provided.

Figure 8:
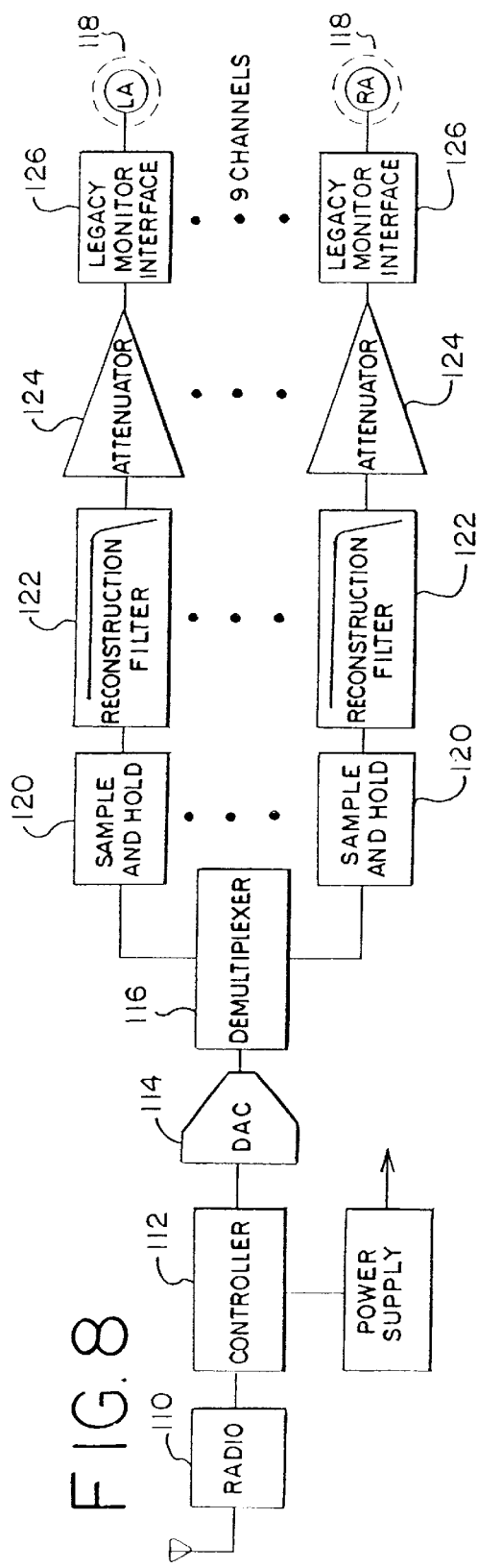
FIG. 8 is a block diagram of one embodiment of a receiver.

FIG. 8 shows one embodiment of the receiver 26. The receiver 26 includes a radio 110, a controller 112, a digital-to-analog converter (DAC) 114, a demultiplexer 116, a plurality of electrode signal channels 118 and a battery or power supply 120. Additional, fewer or different components can be used. Preferably, the power supply 120 comprises a replaceable or rechargeable battery or other power source connected to provide power to the various components of the receiver 26.

The radio 110 demodulates the received signals for identifying digital data representing the combined electrode signals. In one embodiment, the radio 110 also includes a modulator for transmitting control information. The controller 112 controls operation of the various components and may further process the signals from the radio 110, such as interpolating data, converting the signals to digital information, generating control signals for the transmitter 24, operating any user interface, operating any user output or input devices, and diagnosing operation of the system 20. Preferably, the controller 112 in the receiver 26 interpolates the electrode signals to return the effective sample rate to about 3 kHz or another frequency. This enables the reconstruction filters to have a cutoff frequency many times the bandwidth of the electrode signals, thus minimizing any differences in group delay at the frequencies of interest, i.e. less than 150 Hz. The DAC 114 converts the digital signals to analog signals. The demultiplexer 116 separates the individual regenerated electrode signals onto the separate electrode signal channels 118.

In one embodiment, nine electrode signal channels 118 corresponding to the typical nine electrodes used for hexaxial-lead and precordial-lead monitoring. Fewer or additional electrode signal channels 118 can be provided. The electrode signal channels 118 each comprise a sample and hold circuit 120, a filter 122, an attenuator 124 and a connector 126. The sample and hold circuit 120 is controlled by the controller 112 so that the converted electrode signals appear simultaneously on each electrode signal channel 188. Differential error may be mitigated. Other embodiments may include individual DAC's that provide the signals substantially simultaneously. The filter 122 comprises a low pass reconstruction filter for removing high frequency signals associated with the DAC conversion process. The attenuator 124 comprises an amplifier for decreasing the amplitude to a level associated with signals at the electrodes 30, that were earlier amplified in the amplifiers 96 of the transmitter 24. This results in a unity system gain so as not to introduce error between the electrodes and the legacy ECG monitor. Other gains may be used. The connector 126 comprises posts, snaps, plugs, tabs or other electrical connectors for connecting with the lead wire set 70.

The controller 112 sets the demodulation frequency in response to input from the user input device or memory, or the demodulation frequency is fixed. In one embodiment, the user input comprises buttons associated with manual frequency control, with preprogrammed channels, with numbers or characters, with possible transmitters 24 or other input devices for selecting a demodulation frequency. The receiver 26 electrically connects to the ECG monitor 28.

FIG. 6 shows one embodiment of the wireless ECG system 20 where the wires 70 from a standard ECG monitor 28 attach to the electrically conductive posts 72 or other connectors on the receiver 26. The wires 70 comprise a lead-wire set, cable or electrode connectors from or for the ECG monitor 28. The posts 72 are labeled as electrodes 30, and the wires 70 are connected with corresponding outputs on the receiver 26. The receiver 26 outputs signals as if from the corresponding electrodes 30 for processing by the ECG monitor 28. In alternative embodiments, the receiver 26 includes wires for connecting with the ECG monitor 28.

In one embodiment, the receiver 26 physically connects to the ECG monitor 28. For example, latches, clips or straps on the receiver 26 connect the receiver 26 to the ECG monitor 28. In alternative embodiments, the receiver 26 connects to an equipment pole or wall or is free standing. The receiver 26 may be releasably attached. When a patient is moved, the receiver 26 may be detached and moved adjacent a different ECG monitor. Alternatively, different receivers 26 operate with the same transmitter 24, so another receiver 26 is programmed to receive signals from the transmitter 24 on the patient.

The ECG monitor 28 comprises one or more of a bedside monitor, a transport monitor or a discrete (i.e. diagnostic) monitor. Bedside and transport monitors are used for continuous monitoring, such as associated with hexaxial-lead monitoring. A discrete monitor typically is used periodically for analysis, such as associated with "12-lead" monitoring or obtaining multiple vectors associated with precordial and/or hexaxial leads. The ECG monitor 28 processes the electrode signals as if the signals where received directly from the electrodes 30. Neither of the transmitter 24 or receiver 26 includes differential amplifiers for determining a heart vector associated with two electrodes.

Some ECG monitors 28 test for failure or malfunction of electrodes 30. For example, a signal is output on the lead wire to the electrode 30 or a direct current level associated with the signal from the electrode 30 is monitored. To continue to provide this functionality, the wireless ECG system 20 tests for electrode failure or malfunction and indicates the results to the ECG monitor 28. For example, the transmitter 24 performs the same or similar tests as the ECG monitor 28. In other embodiments, the transmitter 24 or receiver 26 determines whether the ECG signal is within an expected range. For example, the controller 112 (FIG. 8) compares the digital electrode signals, such as after interpolation, to maximum and minimum thresholds. If either threshold is exceed by a particular number of samples or for a particular time, a lead-off or faulty electrode 30 is indicated. When one or more samples are subsequently within hysteresis limits of the thresholds, then an error is no longer indicated. When a lead-off condition is indicated, the receiver 26 opens an analog switch or, alternatively does not generate a signal for the output corresponding to the malfunctioning or failed electrode 30. As a result, the ECG monitor 28 indicates a failure of the electrode 30. If the transmitter 24 and receiver 26 are out of radio communication range, a lead-off condition is presented to the ECG monitor 28.

The ECG monitoring system 20 is used for continuous hexaxial-lead or occasional precordial-lead or both hexaxial-lead and precordial-lead monitoring. FIG. 5 shows the acts representing use of the system 20.

In act 50, the electrodes 30 are positioned on the patient. For example, electrodes 30 are positioned in hexaxial positions, precordial positions or combinations thereof.

In act 52, the electrode connector 22 and transmitter are positioned. The expandable arms 32 are expanded, such as expanding a portion or all of the expandable arms 32. Another portion of the expandable arms 32 may remain folded or unexpanded. The expandable arms 32 are expanded to reach one or more electrodes.

In act 54, the electrode connector 22 is connected with the electrodes 30. For example, the expandable arms 32 are releasably connected with one or more electrodes 30, such as snapping or clipping to the electrodes 30. Expandable arms 32 may also be connected with other expandable arms 32, hubs 40, the transmitter 24, and/or the belt 42. In an alternative embodiment, the electrodes 30 are connected with the electrode connector 22 prior to positioning the electrodes 30 and expanding the expandable arms 32.

In act 56, the transmitter 24 is operated or turned-on. In one embodiment, a switch on the transmitter 24 activates the transmitter. In alternative embodiments, connection to one or more of the wires 36, expandable arms 32, electrode connecter 22 and/or electrodes 30 activates the transmitter 24. In response, the transmitter 24 radiates a signal representing the electrode signals.

In act 58, the receiver 26 is programmed. A code corresponding to the transmitter 24 is entered, or a channel (i.e. frequency) is selected. In an alternative embodiment, the receiver 26 searches a plurality of frequencies for an appropriate signal, such as a signal in an expected format or with a particular code. If more than one signal is identified, an output may be provided for user selection of the appropriate signal. A visual or audible output indicating reception of a signal may be provided.

In act 60, wires or electrode connectors from the ECG monitor 28 are connected to the receiver 26. In alternative embodiments, act 60 occurs before any of acts 50, 52, 54, 56 or 58.

In act 62, the ECG device, such as a monitor, printer or memory, is activated. Analog or digital signals corresponding to signals at the electrodes 30 are received by the ECG device from the receiver 26. The ECG device processes the signals to generate ECG data, such as one or more heart vectors.

In one embodiment, a light emitting diode, a light pipe or multiple light emitting diodes, or other output device is provided on the transmitter 24 and/or one or more of the expandable arms 32. The output device indicates electrical operation of the transmitter or conductance of signals by the wire 36. Different output devices may represent improper operation. In one embodiment, extending the expandable arm 32 activates operation of the output device or devices.

The wireless ECG system 20 provides for fewer artifacts due to wire movement, allows the patient to wear clothing without interfering with wires, and provides less psychological intimidation of the patient due to wire connections to a machine. The electrodes 30 are less likely to disconnect because of lower mass or force due to wires connected to the ECG monitor 28. The wireless ECG system 20 is usable with many different ECG monitors 28 and electrodes 30. Faster setup when a patient is transferred and connected to a different ECG monitor 28 is provided since the same electrodes 30 already positioned on the patient can be used. Since the electrodes 30 are not repositioned due to a transfer, the ECG monitor output is more comparable to the output of previous ECG monitors. If an electrode 30 fails because of patient movement or perspiration, the electrode can be replaced without replacing the electrode connector 22 or other electrodes 30.

While the invention has been described above by reference to various embodiments, it will be understood that many changes and modifications can be made without departing from the scope of the invention. For example, the transmitter and receiver may each comprise transceivers for two-way communication and control. Various aspects can be used with or without other aspects, such as using the electrode connector 22 with a transmitter that processes the electrode signals into ECG vector data rather than transmitted signals representing the electrode signals. Another example is transmitting the electrode signals but using a different electrode connector, strip, patch or mere wires. Other biomedical systems, such as temperature or blood pressure, can be additionally or alternatively monitored using the systems and methods discussed above.

It is therefore intended that the foregoing detailed description be understood as an illustration of the presently preferred embodiments of the invention, and not as a definition of the invention. It is only the following claims, including all equivalents that are intended to define the scope of this invention.

What is claimed is:

1. An electrode connector for ECG monitoring of a patient, the connector comprising:
   material operable to interconnect a plurality of electrodes; and
   a plurality of electrode releasable connectors provided on the material
   wherein the material comprises a plurality of expandable arms, each of the plurality of expandable arms corresponding to respective ones of the plurality of electrode releasable connectors.

2. The connector of claim 1 wherein the plurality of expandable arms comprise at least four expandable arms associated with hexaxial electrodes.

3. The connector of claim 1 wherein each of the plurality of expandable arms includes an electrical conductor.

4. The connector of claim 3 wherein each of the electrical conductors electrically connects with the respective electrode releasable connector.

5. The connector of claim 1 wherein each of the expandable arms includes a first portion operable to unfold for expansion and a second portion remaining folded for expansion, the first and second portions based on an amount of expansion.

6. The connector of claim 1 wherein at least a first of the plurality of expandable arms corresponds to a hexaxial electrode and at least a second of the plurality of expandable arms corresponds to a precordial electrode.

7. The connector of claim 6 wherein the second expandable arm connects to the first expandable arm.

8. The connector of claim 1 further comprising a belt, at least one of the plurality of expandable arms connecting with the belt.

9. The connector of claim 8 wherein a first expandable arm comprises a hexaxial electrode arm connected with the belt and a second expandable arm comprises a hexaxial and precordial electrode arm connected with the belt.

10. The connector of claim 9 wherein a first expandable arm comprises a hexaxial electrode arm connected with the belt and a second expandable arm comprises a hexaxial and precordial electrode arm connected with the belt.

11. The method of claim 10 wherein (a) comprises placing the plurality of electrodes for hexaxial-lead monitoring.

12. The method of claim 10 wherein (a) comprises placing the plurality of electrodes for precordial-lead monitoring.

13. The method of claim 10 wherein (a) comprises placing the plurality of electrodes for both hexaxial-lead and precordial-lead monitoring.

14. The method of claim 10 further comprising:
   (d) transmitting signals from the plurality of electrodes with a radio.

15. The method of claim 10 wherein (c) comprises electrically connecting the plurality of electrodes to the plurality of expandable arms with a snap terminal.

16. The method of claim 10 wherein (b) comprises expanding a first portion of each of the expandable arms and leaving a second portion of each of the expandable arms in an unfolded position.

17. The method of claim 10 further comprising:
   (d) connecting a precordial-lead expandable arm with a hexaxial-lead expandable arm.

18. The method of claim 10 further comprising:
   (d) connecting at least one of the plurality of expandable arms to a belt.

19. A system for monitoring electrical signals generated by a patient, the system comprising:
   a transmitter operable to transmit electrode signals from a plurality of electrodes; and
   a receiver responsive to the transmitter to reproduce the electrode signals, the receiver having an output connector;
   wherein the output connector is operable to connect with electrode lead-wires of an ECG monitor, the output connector having outputs corresponding to specific ones of the plurality of electrodes.

20. The system of claim 19 wherein the receiver generates the electrode signals free of ECG vector processing.

21. The system of claim 19 further comprising:
at least one electrode connector electrically connectable with the transmitter and an electrode.

22. The system of claim 21 wherein the transmitter connects with the electrode connector on a surface of the electrode connector.

23. The system of claim 19 further comprising:
a belt electrically connectable with the transmitter.

24. The system of claim 23 wherein the transmitter connects with the belt on a surface of the belt.

25. The system of claim 19 wherein the receiver comprises a connector operable to hold the receiver to the ECG monitor.

26. A method for monitoring electrical signals generated by a patient, the method comprising the acts of:
(a) receiving signals generated by a patient via a plurality of electrodes;
(b) transmitting information representing the signals received from the plurality of electrodes;
(c) receiving the information;
(d) reconstructing the signals received from the plurality of the electrodes;
(e) connecting existing lead-wires from an ECG monitor to outputs corresponding to specific ones of the plurality of electrodes; and
(f) receiving the reconstructed signals at the ECG monitor.

27. The method of claim 26 wherein (e) comprises clipping the existing lead-wires from an ECG monitor to posts.

28. The method of claim 26 further comprising:
programming a receiver for (c).

29. The method of claim 26 wherein (b) comprises transmitting pursuant to a Bluetooth specification.

30. The method of claim 26 further comprising:
(g) placing a plurality of electrodes on a patient; and
(h) connecting the electrodes to a transmitter.

31. The method of claim 26 wherein the reconstructed signals comprise signals free of vector processing.

32. The method of claim 27 wherein the reconstructed signals comprise signals free of vector processing.

33. The system of claim 32 wherein the single transmitter is operable to condition and amplify the signals from the plurality of electrodes.

34. The system of claim 32 wherein the receiver is operable to connect with existing lead-wires of an ECG monitor.

35. The system of claim 32 wherein the reconstructed signals are free of vector processing and correspond to hexaxial-lead electrode positions.

36. The system of claim 33 wherein the reconstructed signals are free of vector processing and correspond to hexaxial-lead electrode positions.

37. The method of claim 36 further comprising:
(e) connecting a receiver operable to perform (d) with existing lead-wires of an ECG monitor.

38. The method of claim 36 wherein (d) comprises reconstructing the signal free of vector processing.

39. The method of claim 37 wherein (d) comprises reconstructing the signals free of vector processing.

40. The improvement of claim 39 wherein the at least one expandable arm comprises a plurality of expandable arms.

41. The improvement of claim 40 wherein the plurality of expandable arms correspond to hexaxial and precordial electrodes.

42. The improvement of claim 39 wherein the at least one expandable arm comprises an electrode snap connector.

43. The improvement of claim 39 further comprising a radio electrically connected with the at least one expandable arm.

44. The improvement of claim 43 further comprising a radio expandable arm having electrical connections with a plurality of electrodes and the radio.

45. The improvement of claim 44 further comprising a radio expandable arm having electrical connections with a plurality of electrodes and the radio.

46. The method of claim 45 wherein (b) comprises positioning the plurality of expandable arms at hexaxial and precordial positions.

47. The method of claim 45 further comprising:
(c) snapping an electrode to each of the plurality of expandable arms.

48. The method of claim 45 further comprising:
(c) releasably connecting one of the plurality of expandable arms to another of the plurality of expandable arms.

49. The method of claim 48 wherein (c) comprises releasably connecting a precordial expandable arm to a hexaxial expandable arm.

50. The method of claim 45 further comprising:
(c) connecting at least one of the plurality of expandable arms to a belt.

51. The method of claim 45 further comprising:
(c) wirelessly transmitting signals from the plurality of expandable arms.

\* \* \* \* \*

UNITED STATES PATENT AND TRADEMARK OFFICE
CERTIFICATE OF CORRECTION

PATENT NO. : 6,611,705 B2
DATED : August 26, 2003
INVENTOR(S) : Nicholas C. Hopman et al.

It is certified that error appears in the above-identified patent and that said Letters Patent is hereby corrected as shown below:

Title Page
Item [63], Related U.S. Application Data, delete "2001." and substitute -- 2000. -- in its place.

Column 12,
Line 27, delete claim 10 in its entirety, and substitute the following in its place:
-- 10. A method for connecting electrodes for ECG monitoring, the method comprising the acts of:

(a)    placing a plurality of electrodes onto a patient;

(b)    expanding a plurality of expandable arms, one expandable arm provided for each of the plurality of electrodes; and (c)    connecting the plurality of expandable arms to the plurality of electrodes, respectively. --.

Column 13,
Line 32, before "programming" insert -- g --.

Line 42, delete claim 32 in its entirety, and substitute the following in its place:
-- 32. A wireless ECG monitoring system for reconstructing signals at a plurality of electrodes, the system comprising:

an electrode connector operable to connect with the plurality of electrodes;

a single transmitter operable to connect with the electrode connector, the single transmitter operable to transmit signals from the plurality of electrodes; and a receiver operable to reconstruct the signals from the plurality of electrodes. --.

Column 14,
Line 4, delete claim 36 in its entirety, and substitute the following in its place:
-- 36. A method for wireless ECG monitoring with reconstructed signals from a plurality of electrodes, the method comprising the acts of:

(a)    connecting the plurality of electrodes with an electrode connector;

(b)    transmitting signals from the plurality of electrodes with a single

UNITED STATES PATENT AND TRADEMARK OFFICE
CERTIFICATE OF CORRECTION

PATENT NO. : 6,611,705 B2
DATED : August 26, 2003
INVENTOR(S) : Nicholas C. Hopman et al.

It is certified that error appears in the above-identified patent and that said Letters Patent is hereby corrected as shown below:

<u>Column 14 (cont'd),</u>
transmitter;

(c)    receiving the signals transmitted by the transmitter; and (d)    reconstructing the signals from the plurality of electrodes. --.

Line 9, delete "signal" and substitute -- signals -- in its place.

Line 11, delete claim 39 in its entirety, and substitute the following in its place:
-- 39.  An improvement of an electrode connector for ECG monitoring of a patient, the improvement comprising:

at least one expandable arm associated with an electrode, the at least one expandable arm comprising a memory less material. --.

Line 26, delete claim 45 in its entirety, and substitute the following in its place:
-- 45.  A method of interconnecting a plurality of electrodes for ECG monitoring, the method comprising the acts of:

(a)    expanding a plurality of expandable arms of memory less material; and (b)    positioning the plurality of expandable arms at electrode positions. --.

Signed and Sealed this

Thirteenth Day of April, 2004

JON W. DUDAS
*Acting Director of the United States Patent and Trademark Office*